(12) United States Patent
Moriizumi et al.

(10) Patent No.: US 8,012,916 B2
(45) Date of Patent: Sep. 6, 2011

(54) PHOSPHORUS-MOLYBDENUM COMPOUND, METHOD FOR PRODUCING SAME AND LUBRICANT ADDITIVE AND LUBRICANT COMPOSITION CONTAINING THE COMPOUND

(75) Inventors: Yukiya Moriizumi, Tokyo (JP); Kazuhiro Umehara, Tokyo (JP); Yukio Tatsumi, Tokyo (JP)

(73) Assignee: Adeka Corporation, Tokyo (JP)

( * ) Notice: Subject to any disclaimer, the term of this patent is extended or adjusted under 35 U.S.C. 154(b) by 239 days.

(21) Appl. No.: 12/311,319

(22) PCT Filed: Oct. 26, 2007

(86) PCT No.: PCT/JP2007/070909
§ 371 (c)(1),
(2), (4) Date: Mar. 26, 2009

(87) PCT Pub. No.: WO2008/053803
PCT Pub. Date: May 8, 2008

(65) Prior Publication Data
US 2009/0270289 A1    Oct. 29, 2009

(30) Foreign Application Priority Data
Oct. 30, 2006   (JP) ................... 2006-294455

(51) Int. Cl.
*C10M 137/10*   (2006.01)
*C07F 9/02*     (2006.01)
(52) U.S. Cl. ............. 508/370; 508/379; 556/24

(58) Field of Classification Search ............. 508/370, 508/379; 556/24
See application file for complete search history.

(56) References Cited

U.S. PATENT DOCUMENTS
2004/0242780 A1* 12/2004 Rademacher et al. ........ 525/191
2005/0107269 A1*  5/2005 Yagishita et al. ............. 508/440
2006/0111256 A1*  5/2006 Kinoshita et al. ............ 508/552

\* cited by examiner

*Primary Examiner* — Glenn Caldarola
*Assistant Examiner* — Vishal Vasisth
(74) *Attorney, Agent, or Firm* — Wenderoth, Lind & Ponack, L.L.P.

(57) ABSTRACT

A lubricating oil additive capable of providing an antioxidant which enables a lubricating oil composition to have long drain intervals, while reducing specific components such as metals and phosphorus atoms, and a lubricating oil composition containing the lubricating oil additive are provided. A phosphorus molybdenum compound represented by the following general formula (1)

[Chemical Formula 1]

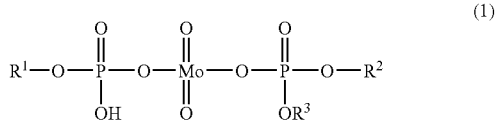

where $R^1$, $R^2$, and $R^3$ each independently represent a hydrocarbon group having 1 to 20 carbon atoms is also provided.

7 Claims, 1 Drawing Sheet

FIG. 1

PHOSPHORUS-MOLYBDENUM COMPOUND, METHOD FOR PRODUCING SAME AND LUBRICANT ADDITIVE AND LUBRICANT COMPOSITION CONTAINING THE COMPOUND

This application is a U.S. national stage of International Application No. PCT/JP2007/070909 filed Oct. 26, 2007.

TECHNICAL FIELD

The present invention relates to a lubricating oil additive containing a phosphorus-molybdenum compound and phosphorous-molybdenum-amine compound having a high antioxidant ability, and a lubricating oil composition containing both.

BACKGROUND ART

There are various problems about lubricating oil compositions due to recent environmental concerns or the like. In particular, there are problems such as prolongation of the life (long drain intervals) of a lubricating oil composition and reduction of specific components (mainly phosphorus atoms) in the lubricating oil composition. The long drain intervals of a lubricating oil composition and reduction of its specific components have been promoted because the long drain intervals are aimed at more efficient use of resources, and reduction of specific components is aimed at safe and economical disposal of a lubricating oil, or in the case where the composition is used as an engine oil, the protection of exhaust gas catalysts is aimed at.

For the long drain intervals of the lubricating oil composition and reduction of its specific components, it is most important to improve the antioxidant ability of the lubricating oil. In particular, lubricating oils such as engine oil or the like may be degraded by heat, moisture, nitric oxide gas or the like, and hence it is essential to improve the antioxidant ability to attain the long drain intervals of the lubricating oil. Therefore, to improve the ability by known antioxidants, the amount of the antioxidant added should then be increased. However, the compound most frequently used as an antioxidant for a lubricating oil is zinc dithiophosphate. Zinc dithiophosphate contains zinc atoms as metals and phosphorus atoms, and it was impossible to reduce the metals or phosphorus atom when the antioxidant (zinc dithiophosphate) was used in larger amounts. Antioxidants such as phenol- and amine-based antioxidants contain no metals and phosphorus atoms, but increases in the addition amounts of the antioxidants cause sludge, etc., so it was impossible to increase the amounts of the antioxidants more than predetermined amount, and the two purposes, the long drain intervals and reduction of specific components such as metals and phosphorus atoms, have not been simultaneously achieved until now.

To solve the problems, various antioxidants have been studied. For example, Patent Document 1 discloses an antioxidant for a lubricant including a styrenated diphenylamine-based compound containing compounds represented by the following formulae (I) and (II) in a total amount of not less than 60 wt %.

[Chemical Formula 1]

Patent Document 2 discloses an antioxidant composition wherein said composition remains in a liquid state even at 0° C. for at least 1 week, which includes 30 to 90% by weight of 2,4-dimethyl-6-t-butyl phenol and 10 to 70% by weight of an alkyl phenol represented by the formula (I):

[Chemical Formula 2]

where $R^1$ and $R^2$ are the same or different and represent hydrocarbon groups having 1 to 18 carbon atoms, X represents at least one kind of a bonding part or a substituent selected from the group consisting of hydrocarbon groups having 1 to 22 carbon atoms, which may contain at least one kind of nitrogen, oxygen, sulfur, and halogen atoms, ester-bond, amide-bond, and sulfide-bond containing groups, m and m' are the same or different and are each 1 or 2, n and n' are the same or different and are each 0 or an integer of 1 to 5, and s, t, and u are the same or different and are each 0 or an integer of 1 to 5, but at least two of them do not represent 0 at the same time.

Further, Patent Document 3 discloses a lubricating composition containing, as essential components, an oil-soluble molybdenum compound obtained by reacting one or two or more hexavalent molybdenum compounds selected from molybdenum trioxide, molybdic acid, and alkali salts thereof with a monophosphate or a diphosphate, and a sulfur-containing compound.

Further, Patent Document 4 discloses a lubricating composition containing, as essential components, an oil-soluble molybdenum compound obtained by reacting one or two or more compounds selected from molybdenum trioxide, molybdic acid, and alkali salts thereof with a reducing agent, and then reacting the resultant compound with a monophosphate or a diphosphate; and a sulfur-containing compound.

Patent Document 1: JP 9-53087 A
Patent Document 2: JP 2004-83868 A
Patent Document 3: JP 62-43491 A
Patent Document 4: JP 62-39696 A

DISCLOSURE OF THE INVENTION

Problems to be Solved by the Invention

However, even if the antioxidants described in Patent Documents 1 and 2 are used, it is impossible to simultaneously attain both long drain intervals of a lubricating oil and reduction of its specific components such as metals and phosphorus atoms. Moreover, the compounds obtained by reacting a molybdenum compound with a phosphorus compound, described in Patent Documents 3 and 4, had an insufficient antioxidant ability and were not able to satisfy the performance required of recent lubricating oil compositions.

Therefore, an object of the present invention is to provide a lubricating oil additive capable of providing an antioxidant which can simultaneously attain both longer drain intervals of a lubricating oil composition and reduction of its specific components such as metals and phosphorus atoms, and a lubricating oil composition containing the additive.

Means for Solving the Problems

The inventors of the present invention have made extensive studies on a compound having an antioxidant ability necessary for recent lubricating oil compositions, and the inventors have found out that a specific phosphorus molybdenum compound has an excellent antioxidant ability, thereby completing the present invention.

The present invention includes a phosphorus molybdenum compound represented by the following general formula (1):

[Chemical Formula 3]

(1)

where $R^1$, $R^2$, and $R^3$ each independently represent a hydrocarbon group having 1 to 20 carbon atoms.

The present invention includes a method of producing the above-mentioned phosphorus molybdenum compound, characterized by including: reacting a hexavalent inorganic molybdenum compound with an acidic monophosphate and an acidic diphosphate.

Further, the present invention includes a lubricating oil additive characterized by including the above-mentioned phosphorus molybdenum compound.

In addition, the present invention includes a lubricating oil additive characterized by including a phosphorus molybdenum amine compound obtained by reacting the above-mentioned phosphorus molybdenum compound with an amine compound.

Further, the present invention includes a lubricating oil composition characterized by being produced by blending the above-mentioned lubricating oil additive in a lubricating base oil.

BEST MODE FOR CARRYING OUT THE INVENTION

An object of the present invention is to simultaneously attain long drain intervals of a lubricating oil and the reduction of specific compounds such as metals and phosphorus atoms. To achieve this, a high-performance antioxidant is included in a lubricating oil. Here, the phosphorus molybdenum compound and phosphorus molybdenum amine compound, which can be used in the lubricating oil additive of the present invention, contain molybdenum and phosphorus atoms, and the addition of those compounds in small amounts can reduce the amount of other metal-containing additives, resulting in a significant reduction of specific components such as metals and phosphorus atoms as compared with a conventional lubricant.

The phosphorus molybdenum compound of the present invention is a compound represented by the following general formula (1):

[Chemical Formula 4]

(1)

In the general formula (1), $R^1$, $R^2$ and $R^3$ each independently represent a hydrocarbon group having 1 to 20 carbon atoms. Examples of the hydrocarbon group include aliphatic hydrocarbon groups such as alkyl, alkenyl, and cycloalkyl groups; and an aryl group.

Examples of the aliphatic hydrocarbon groups include alkyl groups such as a methyl group, an ethyl group, a propyl group, an isopropyl group, a butyl group, a tertiary butyl group, an amyl group, an isoamyl group, a hexyl group, a cyclohexyl group, a heptyl group, an isoheptyl group, an octyl group, an isooctyl group, a 2-ethylhexyl group, a nonyl group, an isononyl group, a decyl group, a dodecyl(lauryl) group, a tridecyl group, a tetradecyl(myristyl) group, a pentadecyl group, a hexadecyl(palmityl) group, a heptadecyl group, and an octadecyl(stearyl) group; alkenyl groups such as a vinyl group, a 1-methylethenyl group, a 2-methyluthenyl group, a propenyl group, a butenyl group, an isobutenyl group, a pentenyl group, a hexenyl group, a heptenyl group, an octenyl group, a decenyl group, a pentadecenyl group, and an octadecenyl group; and cycloalkyl groups such as a cyclohexyl group, a cyclopentyl group, a cyclohexyl group, a cycloheptyl group, a methylcyclopentyl group, a methylcyclohexyl group, a methylcycloheptyl group, a cyclopentenyl group, a cyclohexenyl group, a cycloheptenyl group, a methylcyclopetenyl group, a methylcyclohexenyl group, and a methylcycloheptenyl group.

Examples of the aryl groups include aryl groups such as a phenyl group, a nephthyl group, a 2-methylphenyl group, a 3-methylphenyl group, a 4-methylphenyl group, a 4-vinylphenyl group, a 3-isopropylphenyl group, a 4-isopropylphenyl group, a 4-butylphenyl group, a 4-isobutylphenyl group, a 4-tertiary butylphenyl group, a 4-hexylphenyl group, a 4-cyclohexylphenyl group, a 4-octylphenyl group, a 4-(2-ethylhexyl)phenyl group, and a 4-dodecylphenyl group.

Of these hydrocarbon groups, from the viewpoint of balance of solubility and performance when used in a lubricating oil, the aliphatic hydrocarbon groups having 6 to 18 carbon atoms and aryl groups having 6 to 18 carbon atoms are preferable and aliphatic hydrocarbon groups having 6 to 18 carbon atoms are more preferable.

The phosphorus molybdenum compound represented by the general formula (1) may be produced by any known method, but the compound is preferably produced by reacting a hexavalent inorganic molybdenum compound with an acidic monophosphate and an acidic diphosphate because the production method is easy to carry out and causes less impurities.

Examples of the hexavalent inorganic molybdenum compound to be used in the production of the phosphorus molybdenum compound represented by the general formula (1) include molybdenum trioxide or a hydrate thereof ($MoO_3 \cdot nH_2O$); molybdic acid ($H_2MoO_4$); a metal salt of molybdic acid such as sodium molybdate or potassium molybdate ($M_2MoO_4$; M is a metal atom); ammonium molybdate [$(NH_4)_2MoO_4$ or $(NH_4)_6 (Mo_7O_{24}) \cdot 4H_2O$], $MoOCl_4$, $MoO_2Cl_2$, $MoO_2Br_2$ and $Mo_2O_3Cl_6$. Of these, molybdenum trioxide or a hydrate thereof, a metal salt of molybdic acid, and ammonium molybdate are preferable because they are easily available.

The acidic monophosphate and acidic diphosphate to be used in the production of the phosphorus molybdenum compound represented by the general formula (1) are acidic phosphates represented by the following general formula (2), which include an acidic monophosphate (m=1, n=2) and an acidic diphosphate (m=2, n=1):

[Chemical Formula 5]

(2)

In the general formula (2), R represents a hydrocarbon group having 1 to 20 carbon atoms, m and n denote a number of 1 or 2, and m+n=3. Examples of R include the hydrocarbon groups exemplified in the general formula (1). Note that in the case where m is 2, R's may be the same or different.

Among the hydrocarbon groups, an aliphatic hydrocarbon group having 6 to 18 carbon atoms and an aryl group having 6 to 18 carbon atoms are preferable, and the aliphatic hydrocarbon group having 6 to 18 carbon atoms is more preferable because of the balance between solubility in oil and performance. The molar ratio of the acidic monophosphate and acidic diphosphate is preferably 1/9 to 9/1, more preferably 2/8 to 8/2, still more preferably 4/6 to 6/4. If the acidic monophosphate content is less than 10 mol %, or if the acidic diphosphate content is less than 10 mol %, an antioxidant effect suitable for a lubricating oil may be inferior, and hence the contents described above are not preferred.

The acidic monophosphate and acidic diphosphate may be produced by any known method, for example, by a reaction of an alcohol represented by ROH with phosphoric acid, phosphorus pentoxide, or polyphosphoric acid. If a mixture including an acidic monophosphate and acidic diphosphate is produced, the mixture can be used for a reaction with a hexavalent inorganic molybdenum without further treatment. Meanwhile, in the case where a product containing the acidic monophosphate or acidic diphosphate alone is produced, an acidic monophosphate or an acidic diphosphate may be further mixed with the product, and the resultant mixture may be reacted with a hexavalent inorganic molybdenum compound. Alternatively, the acidic monophosphate and acidic diphosphate may be reacted alternately with a hexavalent inorganic molybdenum. However, the reaction of the mixture of the acidic monophosphate and acidic diphosphate with the hexavalent inorganic molybdenum compound is preferable because the reaction can produce a large amount of the compound represented by the general formula (1).

The reason why the acidic monophosphate and acidic diphosphate are used will be described. The function as an antioxidant is, for example, to slow the progression of degradation by removing a degradation factor by a reaction of a degradation factor such as radicals or peroxide generated in the system with the antioxidant. However, a product obtained by reacting the hexavalent inorganic molybdenum compound with the acidic monophosphate [the compound represented by the general formula (3) is mainly produced] has very high reactivity with the degradation factor and is consumed immediately in the system, and it is difficult to sustain the antioxidant effect. On the other hand, a product obtained by reacting the hexavalent inorganic molybdenum compound with the acidic diphosphate [the compound represented by the general formula (4) is mainly produced] is consumed slowly in the system but has low reactivity with the degradation factor, and hence a high antioxidant effect cannot be achieved. However, if a mixture including the acidic monophosphate and acidic diphosphate is used, the compound represented by the general formula (1) is mainly produced, thereby attaining both high sustainability and a high antioxidant effect. The molar ratio of the acidic monophosphate and acidic diphosphate is preferably 1/9 to 9/1, more preferably 2/8 to 8/2, still more preferably 4/6 to 6/4 because the closer to 1/1 the molar ratio, the larger the produced amount of the compound represented by the general formula (1). Meanwhile, the content of each of the compounds represented by the general formulae (3) and (4) is preferably less than 50 mol %, and more preferably 30 mol % or less with respect to the total amount:

[Chemical Formula 6]

(3)

where $R^4$ and $R^5$ each independently represent a hydrocarbon group having 1 to 20 carbon atoms.

[Chemical Formula 7]

(4)

where $R^6$ to $R^9$ each independently represent a hydrocarbon group having 1 to 20 carbon atoms.

Hereinafter, the method of producing the phosphorus molybdenum compound represented by the general formula (1) will be described in detail. The reaction may be performed by the following two methods: a method involving dissolving or dispersing a hexavalent inorganic molybdenum compound in water, neutralizing the mixture with a mineral acid, and reacting the mixture with an acidic monophosphate and an acidic diphosphate; and a method involving dissolving or dispersing a hexavalent inorganic molybdenum compound in water, reacting the mixture with an acidic monophosphate and an acidic diphosphate, and neutralizing the mixture with a mineral acid. Neutralization with a mineral acid may be performed before or after the reaction with the acidic monophosphate and acidic diphosphate.

Hexavalent molybdenum compounds used as raw materials are solid, and in order to react the acidic monophosphate and the acidic diphosphate, it is necessary to dissolve or disperse the compounds in water. A metal salt of molybdic acid such as sodium molybdate or the like, and ammonium molybdate are water-soluble and can be dissolved in water without further treatment. However, in the case where a water-insoluble molybdenum compound such as molybdenum trioxide is used, an alkaline agent may be added to dissolve the compound. Examples of the alkaline agent include an alkali metal hydroxide such as lithium hydroxide, sodium hydroxide, or potassium hydroxide; and a basic nitrogen compound such as ammonia, monoethanolamine, diethanolamine, or triethanolamine. Of these, sodium hydroxide, potassium hydroxide, and ammonia are preferable because those compounds are easy to handle and inexpensive. The amount of the alkaline agent added is not particularly limited as long as the hexavalent inorganic molybdenum compound can be dissolved or dispersed in water, but in the case of a water-insoluble molybdenum compound such as molybdenum trioxide, the addition amount is preferably 0.5 to 1.5 mol with respect to 1 mol of molybdenum in the system. The amount of water to be used for dissolution is not particularly limited as long as a hexavalent molybdenum compound can be dissolved or dispersed. The amount is preferably adjusted so that the solid content is 10 to 90% by mass. Meanwhile, the temperature for dissolution is 10 to 80° C., preferably 20 to 60° C., more preferably 20 to 40° C.

After the hexavalent inorganic molybdenum compound is dissolved or dispersed in water, if the neutralization step is not performed, an acidic monophosphate and an acidic diphosphate are added and allowed to react. The amount of the acidic monophosphate and acidic diphosphate added is, as a phosphorous atom, 1 to 3 mol, preferably 1.2 to 2.8 mol, more preferably 1.5 to 2.5 mol with respect to 1 mol of molybdenum atom in the system. If the amount of the acidic monophosphate and acidic diphosphate is too small, the hexavalent inorganic molybdenum compound may remain, while if the amount is too large, unreacted acidic monophosphate and acidic diphosphate may remain. Meanwhile, the temperature in the system when the acidic monophosphate and acidic diphosphate are added is preferably 30 to 90° C., and more preferably 30 to 70° C. The acidic monophosphate and acidic diphosphate are gradually added preferably over 0.1 to 3 hours, and more preferably over 0.5 to 2 hours. Further, after addition, aging is performed at 30 to 90° C. for 1 to 20 hours, preferably at 30 to 70° C. for 1 to 20 hours, and more preferably at 30 to 70° C. for 3 to 10 hours. Note that in the case where the neutralization step is performed before the reaction of the acidic monophosphate and acidic diphosphate, the reaction of the acidic monophosphate and acidic diphosphate is performed in the same way as above.

As described above, the neutralization step may be performed before or after the reaction of a hexavalent inorganic molybdenum compound with an acidic monophosphate and an acidic diphosphate. The mineral acid that may be used in the neutralization step may be a monobasic, dibasic, or tribasic acid or a partially-neutralized product thereof, but it is impossible to use a mineral acid containing phosphorus atoms, such as phosphoric acid. Examples of the mineral acid that may be used include hydrochloric acid, nitric acid, sulfuric acid, sulfurous acid, perchloric acid, chloric acid, chlorous acid, and hypochlorous acid. In terms of reaction efficiency and high purity of the product, hydrochloric acid, nitric acid, and sulfuric acid are preferable, and involatile compounds are more preferable because those compounds are easy to handle. Sulfuric acid is particularly preferable.

In the case where the mineral acid is a monovalent acid, the amount of the mineral acid added is 1 to 6 mol, preferably 2 to 5 mol, and more preferably 3 to 5 mol with respect to 1 mol of molybdenum in an aqueous solution. In the case where the mineral acid is a divalent acid, the amount may be half the molar amount of the monovalent acid, while in the case where the mineral acid is a trivalent acid, the amount may be one-third of the molar amount of the monovalent acid. For example, the amount of the divalent acid such as sulfuric acid is 0.5 to 3 mol, preferably 1 to 2.5 mol, and more preferably 1.5 to 2.5 mol with respect to 1 mol of molybdenum in an aqueous solution. If the amount of the mineral acid added is too small, the phosphorus molybdenum compound represented by the general formula (1) is not produced. If the amount of the mineral acid is too large, effects commensurate with the addition amount may not be achieved, and a post-treatment of the mineral acid may be difficult to perform. Thus, too small an amount and too large an amount are not preferred.

Meanwhile, the temperature in the system when the mineral acid is added is preferably 30 to 90° C., and more preferably 40 to 80° C. in the above-mentioned two steps. Further addition of the mineral acid produces heat due to heat of neutralization, and hence the mineral acid is gradually added for safety preferably over 0.1 to 3 hours, and more preferably over 0.5 to 2 hours. Further, after addition, aging is performed at 30 to 90° C. for preferably 0.1 to 5 hours, and more preferably 0.5 to 3 hours.

The phosphorus molybdenum compound represented by the general formula (1) can be produced by the above reaction, but the compound needs to be purified to increase its purity. The purification may be performed by any known method. Examples of the method include a method involving removing water by distillation or the like and removing solid matter obtained as by-products by filtration; a method involving removing water and distilling the phosphorus molybdenum compound represented by the general formula (1); and a method involving extracting the molybdenum compound represented by the general formula (1) with an organic solvent. Of these purification methods, the method of purifying the compound with an organic solvent is preferable because of the ease of the purification process and high purity of the resultant compound.

Specifically, the method of purifying the compound with an organic solvent is performed by, for example, adding an organic solvent that separates from water in the system where the reaction has been completed, stirring the mixture, and allowing the resultant mixture to stand to separate into two phases. The aqueous phase may be the upper phase or the lower phase. In both cases, the aqueous phase is removed, and then the organic solvent in the resultant organic solvent phase is removed under reduced pressure, to thereby produce the phosphorus molybdenum compound represented by the general formula (1). In order to reduce by-products or impurities, water is preferably further added to the resultant organic solvent phase to wash the phase.

The organic solvent that can be used may be any organic solvent that separates from water. Examples thereof include aromatic-based solvents such as benzene, toluene, xylene, hemimellitene, pseudocumene, mesitylene, and cumene; aliphatic hydrocarbon-based solvents such as pentane, hexane, octane, and petroleum ether; ether-based solvents such as dimethyl ether and diethyl ether; and ketone-based solvents such as methyl ethyl ketone and methyl butyl ketone. Of these organic solvents, aromatic-based solvents are preferably used, and benzene, toluene, and xylene are more preferably used because of the ease of separation into the aqueous phase and the organic phase. The use amount of the organic solvent is 20 to 400 parts by mass, preferably 50 to 200 parts by mass with respect to 100 parts by mass of the solid matter in the system. In the case where the solvent is used in the reaction, the use amount of the solvent should be controlled.

The phosphorus molybdenum compound which may be used in the lubricating oil additive of the present invention is that of the above-mentioned phosphorus molybdenum compound represented by the general formula (1) which is reacted with an amine compound. The amine compound to be used in the method of producing a phosphorus molybdenum amine compound of the present invention is not particularly limited as long as the compound has a basic nitrogen atom. Examples thereof include an aliphatic amine, aromatic amine, alkanol amine, polyamine, or a reaction product of a fatty acid with a polyamine.

Examples of aliphatic amines include alkyl amines such as (mono, di, tri)methyl amine, (mono, di, tri)ethyl amine, (mono, di, tri)propyl amine, (mono, di, tri)isopropyl amine, (mono, di, tri)butyl amine, (mono, di, tri)secondary butyl amine, (mono, di, tri)tertiary butyl amine, (mono, di, tri) pentyl amine, (mono, di, tri)isopentyl amine, (mono, di, tri) secondary pentyl amine, (mono, di, tri)tertiary pentyl amine, (mono, di, tri)hexyl amine, (mono, di, tri)secondary hexyl amine, (mono, di, tri)heptyl amine, (mono, di, tri)secondary heptyl amine, (mono, di, tri)octyl amine, (mono, di, tri)2-ethylhexyl amine, (mono, di, tri)octyl amine, (mono, di, tri) secondary octyl amine, (mono, di, tri)nonyl amine, (mono, di, tri)secondary nonyl amine, (mono, di, tri)decyl amine, (mono, di, tri)secondary decyl amine, (mono, di, tri)undecyl amine, (mono, di, tri) secondary undecyl amine, (mono, di, tri)dodecyl amine, (mono, di, tri)secondary dodecyl amine, (mono, di, tri)tridecyl amine, (mono, di, tri)secondary tridecyl amine, (mono, di, tri)tetradecyl amine, (mono, di, tri) secondary tetradecyl amine, (mono, di, tri)hexadecyl amine, (mono, di, tri) secondary hexadecyl amine, (mono, di, tri) stearyl amine, (mono, di, tri)eicosyl amine, (mono, di, tri) docosyl amine; alkenyl amines such as vinyl amine, (mono, di, tri)allyl amine, (mono, di, tri)propenyl amine, (mono, di, tri)isopropenyl amine, (mono, di, tri)butenyl amine, (mono, di, tri)isobutenyl amine, (mono, di, tri)pentenyl amine, (mono, di, tri)isopentenyl amine, (mono, di, tri)hexenyl amine, (mono, di, tri)heptenyl amine, (mono, di, tri)octenyl amine, (mono, di, tri)nonenyl amine, (mono, di, tri)decenyl amine, (mono, di, tri)undecenyl amine, (mono, di, tri)dodecenyl amine, (mono, di, tri)tetradecenyl amine, and (mono, di, tri)oleyl amine.

Examples of aromatic amines include (mono, di, tri)phenyl amine, (mono, di, tri)tolyl amine, (mono, di, tri)xylyl amine, (mono, di, tri)cumenyl amine, (mono, di, tri)benzyl amine, (mono, di, tri)phenetyl amine, (mono, di, tri)styryl amine, (mono, di, tri)trityl amine, (mono, di, tri)ethylphenyl amine, (mono, di, tri)propylphenyl amine, (mono, di, tri)butylphenyl amine, (mono, di, tri)pentylphenyl amine, (mono, di, tri) hexylphenyl amine, (mono, di, tri)heptylphenyl amine, (mono, di, tri)octylphenyl amine, (mono, di, tri)nonylphenyl amine, (mono, di, tri)decylphenyl amine, (mono, di, tri)dodecylphenyl amine, (mono, di, tri)octadecylphenyl amine, (mono, di, tri) styrenated phenyl amine, (mono, di, tri)p-cumylphenyl amine, (mono, di, tri)phenylphenyl amine, (mono, di, tri)benzylphenyl amine, (mono, di, tri)α-naphthyl amine, and (mono, di, tri)β-naphthyl amine.

Examples of alkanol amines include (mono, di, tri)ethanol amine, (mono, di, tri)propanol amine, (mono, di, tri)isopropanol amine, (mono, di, tri)butanol amine, (mono, di, tri) pentanol amine, (mono, di, tri)hexanol amine, (mono, di, tri)octanol amine, (mono, di, tri)nonanol amine, (mono, di, tri)decanol amine, (mono, di, tri)dodecanol amine, (mono, di, tri)tridecanol amine, and (mono, di, tri)octadecanol amine.

Examples of polyamines include ethylene diamine, diethylene triamine, triethylene tetramine, tetraethylene pentamine, pentaethylene hexamine, propylene diamine, dipropylene triamine, tripropylene tetramine, tetrapropylene pentamine, and pentapropylene hexamine.

Examples of fatty acids in the reaction product of a fatty acid with a polyamine include acetic acid, propionic acid, butanoic acid (butyric acid), pentanoic acid (valeric acid), isopentanoic acid (isovaleric acid), hexanoic acid (caproic acid), heptanoic acid, isoheptanoic acid, octanoic acid (caprylic acid), 2-ethylhexanoic acid, isooctanoic acid, nonanoic acid (peralgoic acid), isononanoic acid, decanoic acid (capric acid), isodecanoic acid, undecanoic acid, isoundecanoic acid, dodecanoic acid (lauric acid), isododecanoic acid, tridecanoic acid, isotridecanoic acid, tetradecanoic acid (myristic acid), hexadecanoic acid (palmitic acid), octadecanoic acid (stearic acid), isostearic acid, eicosanoic acid (arachic acid), docosanoic acid (behenic acid), tetracosanoic acid (lignoceric acid), hexacosanoic acid (cerotic acid), octacosanoic acid (montanic acid), 10-undecenic acid, zoomaric acid, oleic acid, elaidic acid, linoleic acid, linolenic acid, gadoleic acid, erucic acid, selacoleic acid, citric acid, succinic acid, fumaric acid, malic acid, alkyl succinic acid, and alkenyl succinic acid. By reaction of those fatty acids with the polyamine, the reaction product of a fatty acid and a polyamine can be obtained. Those reaction products may be amide compounds having amino groups and imide compounds having amino groups.

Of these amine compounds, an aliphatic amine and an imide compound having an amino group are preferable, and an aliphatic amine having an alkyl or alkenyl group having 4 to 18 carbon atoms and an N-substituted alkenyl succinimide are more preferable.

The N-substituted alkenyl succinimide, in which a primary amino group on the end of a polyamine serves as a nitrogen atom in an imide group, may have two structures of mono-succinimide including one imide group and di-succinimide including two imide groups. Such N-substituted alkenyl succinimides include preferably an alkenyl group having a mass average molecular weight of 500 to 3,000 and include more preferably an alkenyl group such as a polypropenyl or polybutenyl group having a mass average molecular weight of 500 to 3,000, because the production thereof is easy.

The above-mentioned reaction of the phosphorus molybdenum compound represented by the general formula (1) with the amine compound may be performed by mixing under stirring both compounds at 50 to 100° C. for 1 to 10 hours; and dehydrating the mixture for 30 minutes to 3 hours at the same temperature as above under reduced pressure.

The lubricating base oil to be used in the lubricating oil composition of the present invention is not particularly limited, and examples thereof include general lubricating base oils that are conventionally used as lubricating base oils, such as mineral oils, synthetic oils, and mixtures thereof. More specific examples of the lubricating base oils include poly-α-olefins, ethylene-α-olefin copolymers, polybutenes, alkylbenzenes, alkylnaphthalenes, polyalkylene glycols, polyphenyl ethers, alkyl-substituted diphenyl ethers, polyol esters, dibasic acid esters, carbonates, silicone oils, fluorinated oils, synthetic oils such as Gas-to-Liquids (GTL), paraffin-based mineral oils, naphthene-based mineral oils, and purified mineral oils obtained by purifying the mineral oils. These base oils may be used alone or as a mixture thereof. Of these lubricating base oils, a base oil having a viscosity index of 100 or more is preferably used, and poly-α-olefins, GTL, and purified mineral oils having a viscosity index of 100 or more are more preferably used.

The lubricating oil composition of the present invention contains the phosphorus molybdenum compound and/or the phosphorus molybdenum amine compound, but two compounds may also be used together. The content of the phosphorus molybdenum compound and/or the phosphorus molybdenum amine compound with respect to the total amount of the lubricating oil composition of the present invention is 10 to 200 ppm by mass, preferably 20 to 100 ppm by mass, and more preferably 30 to 80 ppm by mass in terms of the phosphorus content (total phosphorus content in the case where the composition contains the two compounds). If the content is less than 10 ppm by mass, the effects as an antioxidant may not be achieved, while if the content exceeds 200 ppm by mass, effects commensurate with the addition amount may not be achieved, or sludge may be produced. Thus, those contents are not preferred.

Further, by blending a zinc dithiophosphate represented by the following the general formula (5) in the lubricating oil composition of the present invention, the antioxidant ability can be further improved.

[Chemical Formula 8]

(5)

In the general formula (5), $R^{10}$ and $R^{11}$ each represent hydrocarbon groups. Examples of the hydrocarbon groups include alkyl, alkenyl, aryl, cycloalkyl, and cycloalkenyl groups.

Examples of the alkyl group include methyl, ethyl, propyl, isopropyl, butyl, isobutyl, secondary butyl, tertiaryl butyl, pentyl, isopentyl, secondary pentyl, neopentyl, tertiary pentyl, hexyl, secondary hexyl, heptyl, secondary heptyl, octyl, 2-ethylhexyl, secondary octyl, nonyl, secondary nonyl, decyl, secondary decyl, undecyl, secondary undecyl, dodecyl, secondary dodecyl, tridecyl, isotridecyl, secondary tridecyl, tetradecyl, secondary tetradecyl, hexadecyl, secondary hexadecyl, stearyl, eicosyl, docosyl, tetracosyl, triacontyl, 2-butyloctyl, 2-butyldecyl, 2-hexyloctyl, 2-hexyldecyl, 2-octyldecyl, 2-hexyldodecyl, 2-octyldodecyl, 2-decyltetradecyl, 2-dodecylhexadecyl, 2-hexadecyloctadecyl, 2-tetradecyloctadecyl, and monomethyl branched-isostearyl.

Examples of the alkenyl group include vinyl, allyl, propenyl, isopropenyl, butenyl, isobutenyl, pentenyl, isopentenyl, hexenyl, heptenyl, octenyl, nonenyl, decenyl, undecenyl, dodecenyl, tetradecenyl, and oleyl.

Examples of the aryl group include a phenyl, tolyl, xylyl, cumenyl, mesityl, benzyl, phenetyl, styryl, cinnamyl, benzhydryl, trityl, ethylphenyl, propylphenyl, butylphenyl, pentylphenyl, hexylphenyl, heptylphenyl, octylphenyl, nonylphenyl, decylphenyl, undecylphenyl, dodecylphenyl, styrenated phenyl, p-cumylphenyl, phenylphenyl, benzylphenyl, α-naphthyl, and β-naphthyl groups.

Examples of the cycloalkyl group and cycloalkenyl group include cyclopentyl, cyclohexyl, cycloheptyl, methylcyclopentyl, methylcyclohexyl, methylcycloheptyl, cyclopentenyl, cyclohexenyl, cycloheptenyl, methylcyclopentenyl, methylcyclohexenyl, and methylcycloheptenyl groups.

Of these hydrocarbon groups, $R^{10}$ and $R^{11}$ are preferably alkyl groups, and more preferably secondary alkyl groups. The number of carbon atoms is preferably 3 to 14, more preferably 3 to 10, and most preferably 3 to 8. In addition, $R^{10}$ and $R^{11}$, may be the same or different hydrocarbon groups.

In the case where a=0 in the general formula (5), the compound is referred to as a neutral zinc dithiophosphate (neutral salt), while in the case where a=⅓, the compound is referred to as a basic zinc dithiophosphate (basic salt). The zinc dithiophosphate is a mixture of the neutral salt and basic salt, and hence a represents a number of 0 to ⅓. Although the number of a varies depending on the method of producing a zinc dithiophosphate, the number is preferably 0.08 to 0.3, more preferably 0.15 to 0.3, and most preferably 0.18 to 0.3. If the number of a becomes larger, the stability in hydrolysis may deteriorate, while if the number of a becomes smaller, the abrasion resistance of the blended lubricating oil may deteriorate. Therefore, the zinc dithiophosphate may be appropriately selected depending on the intended use.

The amount added of the zinc dithiophosphate should be determined depending on the amount of the phosphorus molybdenum compound and/or phosphorus molybdenum amine compound added. The zinc dithiophosphate is added so that the total phosphorus content in the lubricating oil composition of the present invention is preferably 800 ppm by mass or less, more preferably 600 ppm by mass or less, and still more preferably 500 ppm by mass or less. If the content exceeds 800 ppm by mass, sludge may be produced, or an exhaust gas catalyst may be adversely affected when the composition is used in gasoline engine oil. Meanwhile, when the total phosphorus content in the lubricating oil composition of the present invention is 100 ppm by mass or less, the antioxidant ability may become insufficient.

When a phenol-based antioxidant and/or an amine-based antioxidant is further blended in the lubricating oil composition of the present invention, the antioxidant ability can be improved. Examples of the phenol-based antioxidant include 2,6-di-tertiary-butylphenol (hereinafter, tertiary butyl is abbreviated as t-butyl), 2,6-di-t-butyl-p-cresol, 2,6-di-t-butyl-4-methylphenol, 2,6-di-t-butyl-4-ethylphenol, 2,4-dimethyl-6-t-butylphenol, 4,4'-methylenebis(2,6-di-t-butylphenol), 4,4'-bis(2,6-di-t-butylphenol), 4,4'-bis(2-methyl-6-t-butylphenol), 2,2'-methylenebis(4-methyl-6-t-butylphenol), 2,2'-methylenebis(4-ethyl-6-t-butylphenol), 4,4'-butylidenebis(3-methyl-6-t-butylphenol), 4,4'-isopropylidenebis(2,6-di-t-butylphenol), 2,2'-methylenebis(4-methyl-6-cyclohexylphenol), 2,2'-methylenebis(4-methyl-6-nonylphenol), 2,2'-isobutylidenebis(4,6-dimethylphenol), 2,6-bis(2'-hydroxy-3'-t-butyl-5'-methylbenzyl)-4-methylphenol, 3-t-butyl-4-hydroxyanisole, 2-t-butyl-4-hydroxyanisole, octyl 3-(4-hydroxy-3,5-di-t-butylphenyl)propionate, stearyl 3-(4-hydroxy-3,5-di-t-butylphenyl)propionate, oleyl 3-(4-hydroxy-3,5-di-t-butylphenyl)propionate, dodecyl 3-(4-hydroxy-3,5-di-t-butylphenyl)propionate, decyl 3-(4-hydroxy-3,5-di-t-butylphenyl)propionate, octyl 3-(4-hydroxy-3,5-di-t-butylphenyl)propionate, tetrakis{3-(4-hydroxy-3,5-di-t-butylphenyl)propionyloxymethyl}methane, 3-(4-hydroxy-3, 5-di-t-butylphenyl)propionic acid glycerin monoester, ester of 3-(4-hydroxy-3,5-di-t-butylphenyl)propionic acid and glycerin monooleyl ether, 3-(4-hydroxy-3,5-di-t-butylphenyl)propionic acid butylene glycol diester, 3-(4-hydroxy-3,5-di-t-butylphenyl)propionic acid thiodiglycol diester, 4,4'-thiobis(3-methyl-6-t-butylphenol), 4,4'-thiobis(2-methyl-6-t-butylphenol), 2,2'-thiobis(4-methyl-6-t-butylphenol), 2,6-di-t-butyl-α-dimethylamino-p-cresol, 2,6-di-t-butyl-4-(N, N'-dimethylaminomethylphenol), bis(3,5-di-t-butyl-4-hydroxybenzyl)sulfide, tris{(3,5-di-t-butyl-4-hydroxyphenyl)propionyl-oxyethyl}isocyanurate, tris(3,5-di-t-butyl-4-hydroxyphenyl)isocyanurate, 1,3,5-tris(3,5-di-t-butyl-4-hydroxybenzyl)isocyanurate, bis(2-methyl-4-(3-n-alkylthiopropionyloxy)-5-t-butylphenyl) sulfide, 1,3,5-tris(4-t-butyl-3-hydroxy-2,6-dimethylbenzyl) isocyanurate, tetraphthaloyl-di(2,6-dimethyl-4-t-butyl-3-hydroxybenzyl-sulfide), 6-(4-hydroxy-3,5-di-t-butylanilino)-2,4-bis(octylthio)-1,3,5-triazine, 2,2-thio-{diethyl-bis-3-(3,5-di-t-butyl-4-hydroxyphenyl)}propionate, N,N'-hexamethylenebis(3,5-di-t-butyl-4-hydroxy-hydrocinnamide, 3,5-di-t-butyl-4-hydroxy-benzyl-phophodiester, bis(3-methyl-4-hydroxy-5-t-butylbenzyl)sulfide, 3,9-bis[1,1-dimethyl-2-{β-(3-t-butyl-4-hydroxy-5-methylphenyl) propionyloxy}ethyl]-2,4,8,10-tetraoxaspiro[5,5]undecane, 1,1,3-tris(2-methyl-4-hydroxy-5-t-butylphenyl)butane, 1,3,5-trimethyl-2,4,6-tris(3,5-di-t-butyl-4-hydroxybenzyl) benzene, and bis{3,3'-bis-(4'-hydroxy-3'-t-butylphenyl)butyric acid}glycol ester.

The phenol-based antioxidant content is preferably 0.01 to 5% by mass, more preferably 0.05 to 4% by mass, and still more preferably 0.1 to 3% by mass with respect to the total amount of the lubricating oil composition of the present invention. If the content is less than 0.01% by mass, the effect of the phenol-based antioxidant may not be achieved, while if the content exceeds 5% by mass, effects commensurate with the amount may not be achieved, or sludge may be produced.

Examples of the amine-based antioxidant include: naphthyl amine-based antioxidants such as 1-naphthyl amine, phenyl-1-naphthyl amine, p-octylphenyl-1-naphthyl amine, p-nonylphenyl-1-naphthyl amine, p-dodecylphenyl-1-naphthyl amine, and phenyl-2-naphthyl amine; phenylenediamine-based antioxidants such as N,N'-diisopropyl-p-phenylene diamine, N,N'-diisobutyl-p-phenylene diamine, N,N'-diphenyl-p-phenylene diamine, N,N'-di-β-nephthyl-p-phenylene diamine, N-phenyl-N'-isopropyl-p-phenylene diamine, N-cyclohexyl-N'-phenyl-p-phenylene diamine, N-1,3-dimethylbutyl-N'-phenyl-p-phenylene diamine, dioctyl-p-phenylene diamine, phenylhexyl-p-phenylene diamine, and phenyloctyl-p-phenylene diamine; diphenyl amine-based antioxidants such as dipyridyl amine, diphenyl amine, p,p'-di-n-butyldiphenyl amine, p,p'-di-t-butylphenylene diamine, p,p'-di-t-pentyldiphenyl amine, p,p'-dioctyldiphenyl amine, p,p'-dinonyldiphenyl amine, p,p'-didecyldiphenyl amine, p,p'-didodecyldiphenyl amine, p,p'-distyryldiphenyl amine, p,p'-dimethoxydiphenyl amine, 4,4'-bis(4-α,α-dimethylbenzoyl)diphenyl amine, p-isopropoxydiphenyl amine, and dipyridyl amine; and phenothiazine-based antioxidants such as phenothiazine, N-methylphenothiazine, N-ethylphenothiazine, 3,7-dioctylphenothiazine, phenothiazine carboxylate, and phenoselenazine.

The amine-based antioxidant content is preferably 0.01 to 5% by mass, more preferably 0.05 to 4% by mass, and still more preferably 0.1 to 3% by mass with respect to the total amount of the lubricating oil composition of the present invention. If the content is less than 0.01% by mass, the effect of the amine-based antioxidant may not be achieved, while if the content exceeds 5% by mass, effects commensurate with the amount may not be achieved, or sludge may be produced. Thus, those contents are not preferred.

Further, the lubricating oil composition of the present invention may contain a known lubricating oil additive, and the composition may further contain an additive such as wear resistance agents, extreme-pressure agents, oiliness improvers, detergents, dispersants, viscosity index improvers, pour-point depressants, rust inhibitors, corrosion inhibitors, or defoaming agents depending on the intended use in amounts that do not impair the effect of the present invention. However, in the case of using a phosphorus-based additive selected from these additives, the total phosphorus content in the engine oil increases, and hence it is necessary to control the content within the range specified in the present invention.

Examples of the wear resistance agents include organic molybdenum compounds such as sulfated oxymolybdenum dithiocarbamate and sulfated oxymolybdenum dithiophosphate. The amount of the wear resistance agent is preferably 30 to 2,000 ppm by mass and more preferably 50 to 1,000 ppm by mass in terms of the molybdenum content with respect to the lubricating base oil. However, sulfated oxymolybdenum dithiocarbamate is preferably used as compared with sulfated oxymolybdenum dithiophosphate containing a phosphorus atom, and sulfated oxymolybdenum dithiocarbamate having an alkyl group having 8 to 13 carbon atoms is more preferably used.

Examples of the extreme-pressure agent include sulfur-based additives such as sulfurized fat and oil, olefin polysulfide and dibenzyl sulfide; phosphorus-based compounds such as monooctyl phosphate, tributyl phosphate, triphenyl phosphite, tributyl phosphite and thiophosphate; and organic metallic compounds such as metal thiophosphate, metal thiocarbamate and acidic metal phosphate. The blending amount of the extreme-pressure agent is preferably 0.01 to 2% by mass and more preferably 0.05 to 1% by mass with respect to the lubricating base oil. However, it is preferable to avoid use of a compound containing phosphorus atoms.

Examples of the oiliness-improver include higher alcohols such as oleyl alcohol and stearyl alcohol; fatty acids such as oleic acid and stearic acid; esters such as oleyl glycerin ester, stearylglycerin ester and laurylglycerin ester; amides such as lauryl amide, oleyl amide and stearyl amide; amines such as lauryl amine, oleyl amine and stearyl amine; and ethers such as lauryl glycerin ether and oleyl glycerin ether. The blending amount of the oiliness-improver is preferably 0.1 to 5 mass % and more preferably 0.2 to 3 mass % with respect to the lubricating base oil.

Examples of the detergent include sulphonates, phenates, salicates and phosphates of calcium, magnesium, and barium, and per basic salts thereof. Of these, the perbasic salts are preferable. Of the perbasic salts, a salt having a total basic number (TBN) of 30 to 500 mg KOH/g is more preferable. Moreover, a salicate-based detergent containing no phosphorus or sulfur atoms is preferable. The blending amount of the detergent is preferably 0.5 to 10% by mass and more preferably 1 to 8% by mass with respect to the lubricating base oil.

Examples of the dispersant include succinimide, succinate or benzylamine, which is added an alkyl or alkenyl group having a weight average molecular weight of about 500 to 3,000, or boron-denatured products thereof. The blending amount of each dispersant is preferably 0.5 to 10% by mass and more preferably 1 to 8% by mass with respect to the lubricating base oil.

Examples of the viscosity index improver include poly(C1-18)alkyl methacrylates, (C1-18)alkyl acrylate/(C1-18) alkyl methacrylate copolymers, diethylaminoethyl methacrylate/(C1-18)alkyl methacrylate copolymers, ethylene/(C1-18) alkyl methacrylate copolymers, polyisobutylenes, polyalkylstyrenes, ethylene/propylene copolymers, styrene/maleate copolymers and styrene/isoprene hydrogenated copolymers. Alternatively, a dispersible or multifunctional viscosity index improver having dispersion performance may be used. The weight average molecular weight is about 10,000 to 1,500,000. The blending amount of the viscosity index improver is preferably 0.1 to 20% by mass and more preferably 0.3 to 15% by mass with respect to the lubricating base oil.

Further, examples of the pour-point depressant include polyalkyl methacrylate, polyalkyl acrylate, polyalkyl styrene and polyvinyl acetate. The weight average molecular weight is 1,000 to 100,000. The blending amount of these pour-point depressants is preferably 0.005 to 3 mass % and more preferably 0.01 to 2 mass % with respect to the lubricating base oil.

Examples of the rust inhibitor include sodium nitrite, oxidized paraffin wax calcium salt, oxidized paraffin wax magnesium salt, beef tallow fatty acid alkali metal salt, alkali earth metal salt or an amine salt, alkenyl succinic acid or alkenyl succinic acid half ester (molecular weight of alkenyl group is about 100 to 300), sorbitan monoester, nonylphenol ethoxylate and lanolin fatty acid calcium salt. The blending amount of these rust inhibitors is preferably 0.01 to 3 mass % and more preferably 0.02 to 2 mass % with respect to the lubricating base oil.

Further, examples of the corrosion inhibitor include benzotriazole, benzoimidazole, benzothiazole and tetraalkylthiuram disulfide. The blending amount of the corrosion inhibitors is preferably 0.01 to 3 mass % and more preferably 0.02 to 2 mass % with respect to the base oil.

Examples of the defoaming agent include polydimethyl silicone, trifluoropropyl methylsilicone, colloidal silica, polyalkyl acrylate, polyalkyl methacrylate, alcohol ethoxy/propoxylate, fatty acid ethoxy/propoxylate and sorbitan partial fatty acid ester. The blending amount of the defoaming agents is preferably 0.001 to 0.1 mass % and more preferably 0.001 to 0.01 mass % with respect to the lubricating base oil.

The lubricating oil composition of the present invention can suppress increases in phosphorus atom content that have various adverse effects while simultaneously enhancing the antioxidant ability. The phosphorus atom content is changed depending on the application and the circumstances in which the composition is used, and it is preferably 800 mass ppm or less with respect to the total amount of the lubricating oil composition.

The lubricating oil composition of the present invention has antioxidant ability for long drain intervals of the composition and exerts the effect of reducing specific components such as metals and phosphorus atoms. Note that the lubricating oil composition of the present invention can be used for lubrication in any application including, for example, lubricating oils such as engine oil, gear oil, turbine oil, hydraulic oil, fire-resistant hydraulic fluid, refrigeration oil, compressor oil, vacuum pump oil, bearing oil, insulating oil, sliding surface oil, rock drill oil, metalworking oil, plastic working oil, heat treating oil and grease. Of these, the lubricating oil composition can be suitably used for engine oil and the turbine oil, which are used in harsh environments and are required to have antioxidant abilities.

EXAMPLES

Hereinafter, the present invention is described more specifically by way of examples. In the following examples, the terms "%" and "ppm" mean "% by mass" and "ppm by mass", respectively, unless otherwise stated.

Compound 1 (Phosphorus Molybdenum Compound)

In a 3,000-ml flask equipped with a nitrogen introduction tube, a reflux tube, a stirrer and a thermometer, 144 g of water were added to 1 mol (144 g) of molybdenum trioxide, and the mixture was heated to 50 to 60° C. under a nitrogen stream. Then, 1 mol (200 g) of 20% sodium hydroxide was added dropwise over 1 hour, and aging was performed for 1 hour. Subsequently, 2 mol (980 g) of 20% sulfuric acid were added dropwise over 1 hour, and aging was further performed for 2 hours. The mixture was cooled to 40 to 50° C., and a mixture of 1 mol (210 g) of mono-2-ethylhexyl phosphate and 1 mol (322 g) of di-2-ethylhexyl phosphate was added dropwise over 1 hour, followed by a reaction for 10 hours. To the resultant was added 300 ml of n-hexane, and the mixture was stirred for 30 minutes. Thereafter, the mixture was allowed to stand for 1 hour to separate the mixture into an aqueous phase and the oil phase, and the aqueous phase was removed. The solvent was removed from the resultant oil phase under reduced pressure, to thereby obtain 630 g of a pale blue oily product. The molybdenum content and the phosphorus content were found to be 13.9% and 9.3%, respectively. The yield of molybdenum was found to be 95%.

Determination of Structure of Compound 1

The molybdenum yield in Compound 1 was found to be 95%, and Compound 1 was purified to remove impurities. Most of the impurities were alcohols produced by decomposition of phosphates. The phosphates were decomposed into alcohol and phosphoric acid, but phosphoric acid produced as an impurity had been removed. Therefore, the alcohol remained in Compound 1 as an impurity. To remove the alcohol (2-ethylhexanol) in Compound 1, the resultant product was heated to 150° C. with stirring to perform removal under reduced pressure at a pressure of 1 kPa for 3 hours.

The results of the elemental analysis for the resultant compound are as follows: Mo=14.5% (theoretical value 14.6%), P=9.4% (theoretical value 9.4%), C=43.7% (theoretical value 43.8%), H=7.9% (theoretical value 7.9%).

Figure 1:
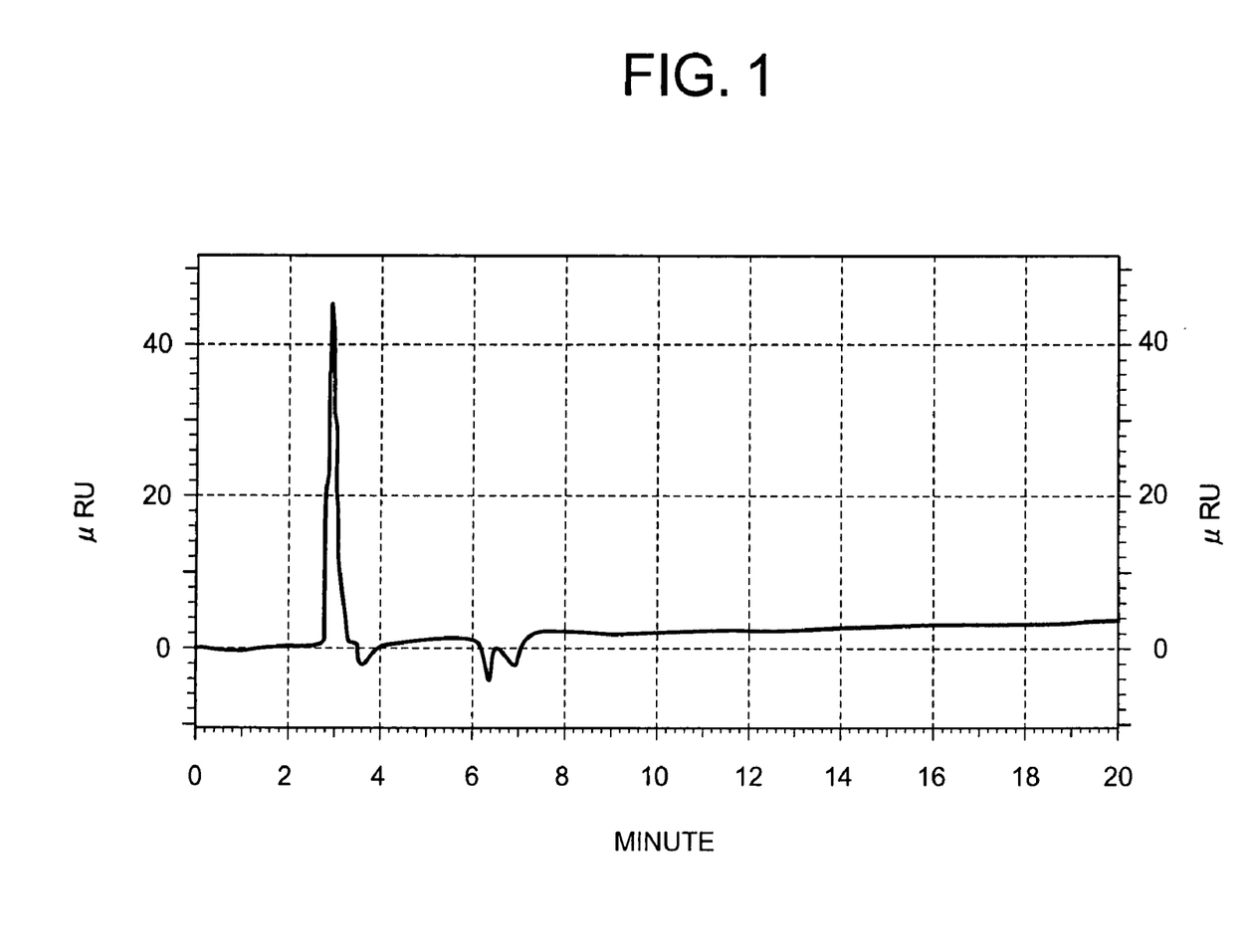
FIG. 1 is a chart of the liquid chromatography analysis for Compound 1.

Thereafter, the resultant compound was analyzed by liquid chromatography. The analysis conditions were as follows:
Apparatus: GL-7400 (GL Sciences Inc.)
Flow rate: 1.0 ml/min
Column: Wakopac, Filler Wakosil 5SIL, $\Phi$4.0 mm×250 mm
Injection volume: 1.0 µl
Detector: RI FIG. 1 is a chart of the liquid chromatography analysis.

The results of the elemental analysis reveal that Compound 1 has the same element ratio as that of the phosphorus molybdenum compound produced by reaction of monophosphate and diphosphate, and the liquid chromatography analysis suggests that Compound 1 includes one component. Therefore, Compound 1 is estimated as a compound represented by the general formula (1) where $R^1$ to $R^3$ represent 2-ethykhexyl groups.

Compound 2 (Phosphorus Molybdenum Compound)

In the same reaction apparatus as in the case of Compound 1, 1 mol (242 g) of sodium molybdate dihydrate was dissolved in 206 g of water, and 2 mol (980 g) of 20% sulfuric acid were added dropwise over 1 hour, followed by aging for 2 hours. After the aging, the mixture was cooled to 30 to 40° C., and 1 mol (348 g) of monooleyl phosphate and 1 mol (598 g) of dioleyl phosphate were added dropwise over 1 hour, followed by a reaction for 10 hours. To the resultant was added 300 ml of n-hexane, and the mixture was stirred for 30 minutes and allowed to stand for 1 hour to separate the mixture into an aqueous phase and an oil phase, followed by removal of the aqueous phase. The solvent was removed from the resultant oil phase under reduced pressure, to thereby obtain 1,027 g of a pale blue oily product. From the results of the analysis of the pale blue oily product, the molybdenum content and the phosphorus content were found to be 8.3% and 5.7%, respectively. The yield of molybdenum was found to be 92%.

From the results of measurement performed in the same way as for Compound 1, Compound 2 was estimated to be a compound represented by the general formula (1) where $R^1$ to $R^3$ represent oleyl groups.

Compound 3 (Phosphorus Molybdenum Compound)

The same procedures for Compound 1 were repeated except for replacing 1 mol of monooctyl phosphate and 1 mol of dioctyl phosphate with 1 mol (238 g) of monodecyl phosphate and 1 mol (598 g) of dioleyl phosphate, to thereby obtain 922 g of a pale blue oily product. The molybdenum content and phosphorus content were found to be 9.5% and 6.3%, respectively. The yield of molybdenum was found to be 95%.

From the results of measurement performed in the same way as for Compound 1, Compound 3 was estimated to be a compound represented by the general formula (1) where $R^1$ represents a decyl group, and $R^2$ and $R^3$ represent oleyl groups.

Compound 4 (Phosphorus Molybdenum Compound)

The same procedures for Compound 1 were repeated except for replacing 1 mol of monooctyl phosphate and 1 mol of dioctyl phosphate with 1 mol (266 g) of monodecyl phosphate and μmol (434 g) of didodecyl phosphate, to thereby obtain 791 g of a pale blue oily product. The molybdenum content and phosphorus content were found to be 11.0% and 7.4%, respectively. The yield of molybdenum was found to be 94%.

From the results of measurement performed in the same way as for Compound 1, Compound 4 was estimated to be a compound represented by the general formula (1) where $R^1$ to $R^3$ represent dodecyl groups.

Compound 5 (Phosphorus Molybdenum Compound)

The procedures for Compound 1 were repeated except for replacing 1 mol of monooctyl phosphate and 1 mol of dioctyl phosphate with 0.6 mol (126 g) of monooctyl phosphate and 1.4 mol (451 g) of dioctyl phosphate, to thereby obtain 673 g of a pale blue oily product. The molybdenum content and phosphorus content were found to be 12.6% and 8.7%, respectively. The yield of molybdenum was found to be 92%.

From the results of measurement performed in the same way as for Compound 1, Compound 5 was estimated to be a compound represented by the general formula (1) where $R^1$ to $R^3$ represent octyl groups, and the compound represented by the general formula (1) includes 40 mol % of the compound represented by the general formula (4) as a by-product.

Compound 6 (Phosphorus Molybdenum Compound)

The procedures for Compound 1 were repeated except for replacing 1 mol of monooctyl phosphate and 1 mol of dioctyl phosphate with 1.4 mol (294 g) of monooctcyl phosphate and 1 mol (193 g) of dioctyl phosphate, to thereby obtain 587 g of a pale blue oily product. The molybdenum content and phosphorus content were found to be 14.8% and 9.9%, respectively. The yield of molybdenum was found to be 94%.

From the results of measurement performed in the same way as for Compound 1, Compound 6 was estimated to be a compound represented by the general formula (1) where $R^1$ to $R^3$ represent octyl groups, and the compound represented by the general formula (1) includes 40 mol % of the compound represented by the general formula (3) as a by-product.

Compound 7 (Phosphorus Molybdenum Compound)

The procedures for Compound 1 were repeated except for replacing 1 mol of monooctyl phosphate and 1 mol of dioctyl phosphate with 1 mol (174 g) of monophenyl phosphate and 1 mol (250 g) of diphenyl phosphate, to thereby obtain 526 g of a pale blue oily product. The molybdenum content and phosphorus content were found to be 15.8% and 11.1%, respectively. The yield of molybdenum was found to be 90%.

From the results of measurement performed in the same way as for Compound 1, Compound 7 was estimated to be a compound represented by the general formula (1) where $R^1$ to $R^3$ represent phenyl groups.

Compound 8 (Phosphorus Molybdenum Compound)

Compound 1 (589 g) was reacted with 1 mol (482 g) of diocutylamine at 60 to 70° C. for 6 hours. Then, the mixture was stirred at a reduced pressure of 2.3 to 1.3 kPa for 1 hour, to thereby obtain 1,006 g of a dark blue oily product. The molybdenum content and phosphorus content were found to be 8.5% and 5.4%, respectively.

Compound 9

Compound 3 (556 g) was reacted with 1.2 mol (737 g) of alkenyl monosuccinimide at 60 to 70° C. for 8 hours. Then, the mixture was stirred at a reduced pressure of 2.3 to 1.3 kPa, to thereby obtain 1,228 g of a dark blue oily product. The molybdenum content and phosphorus content were found to be 6.5% and 4.2%, respectively.

Compound 10 (Phosphorus Molybdenum Compound)

The procedures for Compound 1 were repeated except for replacing 1 mol of monooctyl phosphate and 1 mol of dioctyl phosphate with 2 mol (420 g) of monooctyl phosphate, to thereby obtain 522 g of a pale blue oily product. The molybdenum content and phosphorus content were found to be 16.8% and 11.2%, respectively. The yield of molybdenum was found to be 95%.

From the results of measurement performed in the same way as for Compound 1, Compound 10 was estimated to be a compound represented by the general formula (3) where $R^4$ and $R^5$ represent octyl groups.

Compound 11

The procedures for Compound 1 were repeated except for replacing 1 mol of monooctyl phosphate and 1 mol of dioctyl phosphate with 2 mol (644 g) of dioctyl phosphate, to thereby obtain 737 g of a pale blue oily product. The molybdenum content and phosphorus content were found to be 11.4% and 7.9%, respectively. The yield of molybdenum was found to be 91%.

From the results of measurement performed in the same way as for Compound 1, Compound 11 was estimated to be a compound represented by the general formula (4) where $R^6$ to $R^9$ represent octyl groups.

Compound 12

The procedures for Compound 1 were repeated except for replacing 1 mol of monooctyl phosphate and 1 mol of dioctyl phosphate with 1.85 mol (389 g) of monooctyl phosphate and 0.15 mol (48 g) of dioctyl phosphate, to thereby obtain 538 g of a pale blue oily product. The molybdenum content and phosphorus content were found to be 16.1% and 10.8%, respectively. The yield of molybdenum was found to be 94%.

From the results of measurement performed in the same way as for Compound 1, Compound 12 was estimated to be a compound represented by the general formula (3) where $R^4$ and $R^5$ represent octyl groups.

Compound 13

The procedures for Compound 1 were repeated except for replacing 1 mol of monooctyl phosphate and 1 mol of dioctyl phosphate with 0.15 mol (32 g) of monooctyl phosphate and 1.85 mol (596 g) of dioctyl phosphate, to thereby obtain 721 g of a pale blue oily product. The molybdenum content and phosphorus content were found to be 11.8% and 8.1%, respectively. The yield of molybdenum was found to be 92%.

From the results of measurement performed in the same way as for Compound 1, Compound 13 was estimated to be a compound represented by the general formula (4) where $R^6$ to $R^9$ represent octyl groups.

Compound 14

Zinc Dithiophosphate

In the general formula (5), $R^{10}$ represents a linear butyl group, $R^{11}$ represents a linear octyl group, a represents 0.2, and phosphorous content is 8.2%.

Compound 15
Phenol-Based Antioxidant (2,6-di-t-butyl-p-cresol)
Compound 16
Amine-Based Antioxidant (p,p'-dioctyl diphenyl amine)
Oxidation Degradation Test 1

The above-mentioned Compounds 1 to 14 were blended in 5 g of a base oil in a glass inner cylinder tube in the combinations and amounts described in Tables 1 and 2, and the compounds were dispersed/dissolved by stirring. Then, each mixture was set in a 100-ml autoclave, which was sealed with a lid equipped with a pressure sensor and an exhaust pipe. Air in the autoclave was exhausted via the exhaust pipe using a vacuum pump, and oxygen was supplied so that the autoclave was in a 100% oxygen atmosphere, while adjusting the pressure to 101 kPa. The autoclave was placed in a 160° C. constant-temperature bath, and the pressure was measured every hour with the time between the start of the test and the moment when the pressure reached a level lower than 80 kPa being defined as an oxidation induction period. Oxidation degradation causes a reduction in the pressure due to consumption of oxygen, and hence a longer oxidation induction period suggests that the composition has a high antioxidant ability. Table 2 shows the results. Note that, the 147 kPa at time 0 means that the pressure adjusted to 101 kPa at room temperature in the autoclave was elevated by heating to 160° C. Table 3 shows the results.

The lubricating base oil used was a mineral oil-based high-viscosity-index (VI) oil with kinetic viscosities of 4.24 mm$^2$/sec (100° C.) and 19.65 mm$^2$/sec (40° C.) and a viscosity index of 126.

TABLE 1

| Compound | Example | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 11 | 12 | 13 | 14 |
| 1 | 3 | | | | | | | | | 3 | | | | |
| 2 | | 3 | | | | | | | | | | | | |
| 3 | | | 3 | | | | | | | | 3 | 3 | | |
| 4 | | | | 3 | | | | | | | | | | |
| 5 | | | | | 3 | | | | | | | | 3 | |
| 6 | | | | | | 3 | | | | | | | | 3 |
| 7 | | | | | | | 3 | | | | | | | |
| 8 | | | | | | | | 3 | | | | | | |
| 9 | | | | | | | | | 3 | | | | | |
| 14 | | | | | | | | | | 45 | 45 | 45 | 25 | 25 |
| 15 | | | | | | | | | | | 15 | 15 | | |
| 16 | | | | | | | | | | | | 15 | | |
| Base oil (g) | 5 | 5 | 5 | 5 | 5 | 5 | 5 | 5 | 5 | 5 | 5 | 5 | 5 | 5 |
| Phosphorus content (ppm) | 34 | 56 | 38 | 44 | 52 | 60 | 67 | 32 | 25 | 772 | 776 | 776 | 462 | 470 |

*Amounts of Compounds 1 to 9 and 14 to 16 in mg.

TABLE 2

| Compound | Comparative Example | | | | | | |
|---|---|---|---|---|---|---|---|
| | 1 | 2 | 3 | 4 | 5 | 6 | 7 |
| 10 | 3 | | | | 3 | | |
| 11 | | 3 | | | | 3 | |
| 12 | | | 3 | | | | |
| 13 | | | | 3 | | | |
| 14 | | | | | 45 | 45 | |
| 15 | | | | | 15 | 15 | |
| 16 | | | | | 15 | 15 | |
| Base oil (g) | 5 | 5 | 5 | 5 | 5 | 5 | 5 |
| Phosphorus content (ppm) | 67 | 48 | 65 | 49 | 805 | 786 | 0 |

*Amounts of Compounds 10 to 16 in mg.

TABLE 3

| | | Oxygen pressure at each time point (kPa) | | | | | | | | | |
|---|---|---|---|---|---|---|---|---|---|---|---|
| | | 0 hr | 5 hr | 10 hr | 20 hr | 40 hr | 60 hr | 80 hr | 100 hr | 150 hr | 200 hr |
| Example | 1 | 147 | 146 | 145 | 144 | 142 | 138 | 76 | | | |
| | 2 | 147 | 146 | 144 | 143 | 141 | 136 | 74 | | | |
| | 3 | 147 | 146 | 144 | 143 | 140 | 136 | 73 | | | |
| | 4 | 147 | 146 | 125 | 144 | 141 | 137 | 75 | | | |
| | 5 | 147 | 144 | 142 | 140 | 139 | 128 | 78 | | | |
| | 6 | 147 | 147 | 146 | 145 | 143 | 139 | 72 | | | |
| | 7 | 147 | 145 | 142 | 140 | 138 | 135 | 69 | | | |
| | 8 | 147 | 144 | 143 | 139 | 137 | 134 | 62 | | | |
| | 9 | 147 | 144 | 142 | 138 | 136 | 133 | 60 | | | |

TABLE 3-continued

|  |  | Oxygen pressure at each time point (kPa) | | | | | | | | |
|---|---|---|---|---|---|---|---|---|---|---|
|  |  | 0 hr | 5 hr | 10 hr | 20 hr | 40 hr | 60 hr | 80 hr | 100 hr | 150 hr | 200 hr |
|  | 10 | 147 | 147 | 146 | 145 | 144 | 141 | 138 | 79 | | |
|  | 11 | 147 | 147 | 146 | 145 | 144 | 143 | 141 | 136 | 75 | |
|  | 12 | 147 | 147 | 147 | 146 | 145 | 144 | 143 | 140 | 136 | 79 |
|  | 13 | 147 | 147 | 145 | 142 | 140 | 137 | 123 | 67 | | |
|  | 14 | 147 | 147 | 147 | 146 | 145 | 143 | 135 | 78 | | |
| Comparative | 1 | 147 | 147 | 147 | 146 | 52 | | | | | |
| Example | 2 | 147 | 118 | 100 | 90 | 79 | | | | | |
|  | 3 | 147 | 147 | 146 | 145 | 76 | | | | | |
|  | 4 | 147 | 124 | 119 | 98 | 77 | | | | | |
|  | 5 | 147 | 147 | 147 | 147 | 142 | 136 | 78 | | | |
|  | 6 | 147 | 126 | 118 | 106 | 95 | 84 | 75 | | | |
|  | 7 | 147 | 72 | | | | | | | | |

Oxidation Degradation Test 2

Various additives were blended in the mineral oil-based high-viscosity-index (VI) oil (base oil) with kinetic viscosities of 4.24 mm²/sec (100° C.) and 19.65 mm²/sec (40° C.) and a viscosity index of 126 at the ratios described in Table 4, to thereby obtain an engine oil composition. The compounds of the present invention and compounds for comparison (0.5 parts by mass) were blended in 100 parts by mass of the engine composition, and in conformance with ISOT test specified in the item 4 of JISK 2514-1993 (lubricating oil-oxidation stability testing method), the test oils were degraded. The test was performed as follows: 250 ml of each sample oil was blended into a glass vessel in which a copper plate and an iron plate had been placed as catalysts, and the whole was heated at 165.5° C. for 168 hours to degrade the test oil by oxidation while the sample was stirred at 1,300 rpm in such a manner that air would be involved. After completion of the test, an increase in the total acid number of the degraded oil (a value obtained by subtracting the total acid number of the test oil before degradation from the total acid number of the degraded oil) was determined. An oil with less increase in the total acid number was estimated to have higher oxidative stability. In this test, if the increase in the total acid number exceeds 10 mgKOH/g, the oil is difficult to use as a general engine oil. Table 5 shows the results.

TABLE 4

|  | Engine oil composition |
|---|---|
| Base oil | 100 parts by mass |
| Methacrylate-based viscosity index improver | 3.4 parts by mass |
| Succinimide-based dispersant | 5 parts by mass |
| Sulfonate-based cleaning agent | 2.5 parts by mass |
| Compound 14 | 0.6 part by mass |
| Compound 15 | 0.25 part by mass |
| Compound 16 | 0.25 part by mass |
| Phosphorus content (ppm by mass) | 439 |

TABLE 5

|  | Compound | Amount of compound (parts by mass) | Phosphorus content (ppm by mass) | Increase in total acid value (mgKOH/g) |
|---|---|---|---|---|
| Example | Compound 1 | 0.5 | 485 | 3.8 |
|  | Compound 5 | 0.5 | 482 | 4.5 |
|  | Compound 6 | 0.5 | 488 | 4.8 |
| Comparative | Compound 10 | 0.5 | 495 | 12.4 |
| Example | Compound 11 | 0.5 | 478 | 13.7 |
|  | None | — | 439 | 21.3 |

The invention claimed is:

1. A lubricating oil composition comprising a phosphorus molybdenum compound represented by the following formula (1):

(1)

wherein $R^1$, $R^2$, and $R^3$ each independently represent a hydrocarbon group having 1 to 20 carbon atoms wherein the compound is blended in a lubricating base oil.

2. A lubricating oil additive comprising a phosphorus molybdenum amine compound obtained by reacting a phosphorus molybdenum compound represented by the following formula (1):

(1)

wherein $R^1$, $R^2$, and $R^3$ each independently represent a hydrocarbon group having 1 to 20 carbon atoms, with an amine compound.

3. The lubricating oil composition according to claim 1, further comprising zinc dithiophosphate.

4. The lubricating oil composition according to claim 1, further comprising a phenol-based and/or amine-based antioxidant.

5. The lubricating oil composition according to claim 1, further comprising at least one additive selected from the group consisting of an antiwear agent, an extreme-pressure agent, an oiliness improver, a detergent, a dispersant, a viscosity index improver, a pour-point depressant, a rust inhibitor, a corrosion inhibitor, and a defoaming agent.

6. The lubricating oil composition according to claim 1, wherein the phosphorus content is 800 ppm by mass or less.

7. A method of using a phosphorus molybdenum compound represented by the following formula (1):

(1)

wherein $R^1$, $R^2$, and $R^3$ each independently represent a hydrocarbon group having 1 to 20 carbon atoms, as an antioxidant in a lubricating composition, said method comprising contacting the compound with a lubricating base oil.

* * * * *